(12) United States Patent
Guenter et al.

(10) Patent No.: US 8,985,331 B2
(45) Date of Patent: *Mar. 24, 2015

(54) TRANSFER ELEMENT AND CONTAINER FOR A MEDICAL INSTRUMENT OR IMPLANT, PARTICULARLY FOR A DENTAL IMPLANT

(75) Inventors: Daniel Guenter, Basel (CH); Jost Lussi, Basel (CH); Stephane Courvoisier, Basel (CH)

(73) Assignee: Straumann Holding AG, Basel (CH)

( * ) Notice: Subject to any disclaimer, the term of this patent is extended or adjusted under 35 U.S.C. 154(b) by 536 days.

This patent is subject to a terminal disclaimer.

(21) Appl. No.: 13/387,023

(22) PCT Filed: Jul. 27, 2010

(86) PCT No.: PCT/EP2010/004593
§ 371 (c)(1),
(2), (4) Date: Mar. 29, 2012

(87) PCT Pub. No.: WO2011/012287
PCT Pub. Date: Feb. 3, 2011

(65) Prior Publication Data
US 2012/0181202 A1    Jul. 19, 2012

(30) Foreign Application Priority Data
Jul. 27, 2009  (EP) .................................... 09009674

(51) Int. Cl.
A61J 1/00    (2006.01)
A61C 8/00    (2006.01)

(52) U.S. Cl.
CPC .............. *A61C 8/0087* (2013.01); *A61C 8/0089* (2013.01); *A61C 2202/00* (2013.01)
USPC ....................................................... 206/438

(58) Field of Classification Search
CPC . A61C 8/0087; A61C 8/0089; A61C 2202/00

USPC ........... 206/438; 433/172, 173, 174, 175, 176
See application file for complete search history.

(56) References Cited

U.S. PATENT DOCUMENTS 5,062,800 A * 11/1991 Niznick ......................... 433/229
5,322,443 A *  6/1994 Beaty ............................. 433/141

(Continued)

FOREIGN PATENT DOCUMENTS

EP         1523955 B1    10/2003
WO    2009/147166 A1    12/2009

OTHER PUBLICATIONS

Nov. 26, 2010 International Search Report and Written Opinion in PCT/US2010/004593.

*Primary Examiner* — Steven A. Reynolds
*Assistant Examiner* — King M Chu
(74) *Attorney, Agent, or Firm* — Novak Druce Connolly Bove + Quigg LLP

(57) ABSTRACT

Transfer element (1) and a container for a medical instrument or implant, more particularly for a dental implant (25). The transfer element (1) includes an adapter segment (10) for holding the medical instrument or implant and for attaching the transfer element (1) to a housing of a container, and also a means for handling the medical instrument or the implant by hand and/or with the aid of an auxiliary tool, and, optionally, a holder segment (5) arranged on the first end (7) and connected to the adapter segment (10). The adapter segment (10) has an adapter end region (20) for detachably holding the medical instrument or implant and a connection section (15). The connection section (15) has connection means that are intended to interact with corresponding connection means of the housing. The means for handling the medical instrument or implant by hand and/or by means of an auxiliary tool are arranged on the connection section (15) and/or, optionally, on the holder segment (5).

20 Claims, 5 Drawing Sheets

(56) References Cited

U.S. PATENT DOCUMENTS

| | | | |
|---|---|---|---|
| 5,829,591 A | * | 11/1998 | Lyons ............................ 206/373 |
| 5,873,722 A | * | 2/1999 | Lazzara et al. ................ 433/173 |
| 6,261,097 B1 | | 7/2001 | Schmutz et al. |
| 2006/0105296 A1 | * | 5/2006 | Linder et al. .................. 433/173 |
| 2006/0269890 A1 | | 11/2006 | Mundwiler et al. |
| 2007/0193905 A1 | * | 8/2007 | Jemelin et al. ................ 206/438 |

\* cited by examiner

TRANSFER ELEMENT AND CONTAINER FOR A MEDICAL INSTRUMENT OR IMPLANT, PARTICULARLY FOR A DENTAL IMPLANT

FIELD OF THE INVENTION

The present invention relates to a transfer element and a container for a medical instrument or implant, more particularly for a dental implant.

BACKGROUND

Medical instruments or implants, more particularly dental implants, are often provided to the medical or dental practitioner in a sterile state. In order to ensure the sterile state during transport and storage, the packaging of the implant must have a sterile barrier, which is often formed by an outer packaging element. Moreover, the packaging of implants, more particularly of dental implants, has a further packaging element that protects the implant from mechanical influences, in particular abrasion. Containers are used as further packaging element and these moreover protect the implant from unnecessary contact with other materials, which could chemically contaminate or inactivate the surface of the implant.

Implants are usually held with an auxiliary tool, which allows or should ease the insertion of the implant in the patient. Thus, for example, dental implants are often held by means of a (screw-in) adapter and screwed into the bone with the aid of a socket wrench. Suitable containers should therefore ensure that the implant is not contaminated chemically, biologically or by particles or excessively loaded by germs during the removal from the container and the insertion into the auxiliary tool.

EP-A-1 749 501 discloses a holding element for a dental implant, comprising an engagement segment suitable for engaging with a processing tool, an attachment segment suitable for being attached to a packaging and a clamping segment suitable for attaching a dental implant on the holding element. The clamping segment has a force-transmission element and a clamping element.

U.S. Pat. No. 6,261,097 B1 describes a holding element that can be screwed into a female thread of a bore hole in an implant. The holding element serves to mount the implant in the interior of an ampoule and to apply a screwing-in tool during the implantation.

SUMMARY OF THE INVENTION

It is an object of the present invention to provide a container for a medical instrument or implant, more particularly a dental implant, which protects the instrument or implant during transport from mechanical influences and thus serves as a transport safety device for the instrument or for the implant. It should be possible to remove the instrument or the implant from the container in a very simple fashion and this is able to be carried out such that the risk of contamination of the instrument or of the implant is reduced. Moreover, the container should be embodied such that the instrument or the implant has as few contact areas with the container as possible such that sterilization of the instrument or of the implant can be brought about in a simpler fashion and the risk of contamination by the container of the surface of the instrument or of the implant is reduced.

According to the present invention, the transfer element for a medical instrument or for a medical implant, more particularly a dental implant, comprises a longitudinal axis, a first and a second end, an adapter segment, arranged on the second end, for holding the medical instrument or implant and for attaching the transfer element to a housing of a container for the medical instrument or implant. The transfer element moreover comprises means for handling the medical instrument or the implant by hand and/or with the aid of an auxiliary tool, and, optionally, a holder segment arranged on the first end and connected to the adapter segment. The first end, the second end, the adapter segment and the optional holder segment are arranged on the longitudinal axis. The adapter segment has an adapter end region, arranged on the second end, for detachably holding the medical instrument or implant and a connection section, arranged between the adapter end region and the first end or the holder segment. The connection section has connection means that are intended to interact with corresponding connection means of the housing. The means for handling the medical instrument or implant by hand and/or by means of an auxiliary tool are arranged on the connection section and/or, optionally, on the holder segment.

The transfer element according to the invention makes simple handling of the medical instrument or implant possible. In particular, the means for handling allow a simple removal of the medical instrument or implant by hand and/or with the aid of the auxiliary tool.

In a preferred embodiment, the transfer element comprises the holder segment. The holder segment is preferably embodied such that it at least partly projects beyond the housing when the transfer element is connected to the housing; however, at the very least it is accessible from the outside. This guarantees simple handling of the transfer element.

The means for handling the medical instrument or implant by hand and/or with the aid of an auxiliary tool are preferably arranged on the holder segment. Hence, the means for handling are easily accessible and allow simple picking up or simple interaction with the auxiliary tool, and secure holding.

In a further preferred embodiment, the means for handling by hand are arranged on the holder segment and the means for handling with the aid of an auxiliary tool are arranged on the connection section.

In a particularly preferred embodiment, the means for handling the medical instrument or the implant are embodied such that they are suitable for inserting an implant, more particularly a dental implant, into an implantation site by hand and/or with the aid of an auxiliary tool, more particularly by means of a screwing-in tool. As a result, a dental implant can be picked up by hand and/or with the auxiliary tool directly or indirectly via the transfer element, even if it is still fixedly connected to the housing and still protected by the container, and it can be at least partly inserted into the implantation site without having to replace the auxiliary tool by another tool.

The means for handling the medical instrument or implant, more particularly for inserting the implant, by hand and/or by means of the auxiliary tool are preferably selected from the group consisting of ribs, notches, a handle, a screw thread, an internal or external Torx, a slit and an internal or external polygon, more particularly a hexagon or an octagon, and combinations thereof. The means can be arranged both on an inner side, e.g. in a bore, of the holder segment or of the connection section and also on an outer side of the holder segment or of the connection section.

Prior to removal, the implant is usually situated in the housing of the container, wherein the implant is connected to the adapter end region of the transfer element. In a preferred embodiment, the transfer element is mounted on an open end face of the housing such that the holder segment with the means for handling comes to rest outside of the housing. Said embodiment allows simple picking up of the holder segment by hand. In order to insert the implant into an implantation site, the transfer element is removed from the housing together with the implant. The means for handling on the holder segment make a simple removal of the implant from the container possible, preferably without the implant coming into contact with other objects, in particular without coming into contact with the hands of the user, and possibly being contaminated. The implant is subsequently brought to the implantation site with the aid of the transfer element. The means of the holder segment for inserting the implant allow the user to pick up the implant with his fingers—without further aids—and then to transfer it to the implantation site and mount it there, for example by turning or pressing. The means for handling the medical instrument or implant by hand preferably comprise ribs, notches or a handle.

In particular, the means for handling make it possible to screw an implant, more particularly a dental implant, at least partly into a bore hole in a bone only using fingers—without further aids—particularly if the means are arranged on the holder segment of the transfer element.

Alternatively, the means for handling make direct interaction between the auxiliary tool and the medical instrument or implant possible. Moreover, it is possible to remove the transfer element, for example with the aid of the auxiliary tool, before further screwing in of the implant.

In a preferred embodiment, the transfer element allows an auxiliary tool to be mounted to the means for handling the medical instrument or implant such that the transfer element can subsequently be removed from the container together with the medical instrument or implant with the aid of the auxiliary tool. In the case of an implant, the implant and the transfer element are then normally transferred to the implantation site with the aid of the auxiliary tool and are attached there, in particular by screwing in. The means for handling the medical instrument or implant with the aid of an auxiliary tool preferably comprise a screw thread, a Torx, a slit or an internal or external polygon, more particularly a hexagon or an octagon.

A particularly preferred embodiment has both means for handling by hand and also means for handling with the aid of an auxiliary tool. Said embodiment makes possible the removal, the transfer and/or the mounting, more particularly the screwing in of the implant, both by means of an auxiliary tool and also by hand. It is conventional for the removal, the transfer and a first stage of mounting the implant, more particularly a first stage of screwing in, to be brought about by hand and for a second stage of mounting the implant, more particularly a second stage of screwing in, to be brought about with the aid of an auxiliary tool in order to be able to generate stronger forces for attaching the implant. Since the first stage can be carried out by hand, mounting the implant is made easier. Moreover, it is made possible for the user to make a better estimate of the forces acting on the implant and the implantation site. The means for handling subsequently make it possible to screw the implant further into the bone by means of an auxiliary tool.

The transfer element is preferably designed as a hollow cylinder in order to simplify or allow possible interaction between the auxiliary tool and the transfer element. The adapter segment in particular preferably substantially has the shape of a hollow circular cylinder with an outer lateral face. Moreover, the first end of the transfer element is preferably open, i.e. the holder segment or the connection section has a recess, preferably centrally arranged, along the longitudinal axis. This allows the auxiliary tool to be inserted into the transfer element and thus allows the auxiliary tool to interact with the means for handling.

A preferred embodiment of the transfer element with a passage bore along the longitudinal axis renders it possible for the auxiliary tool to be inserted into the transfer element and thus interact directly with the medical instrument or implant. In particular, this affords the possibility of a direct force transmission, for example a direct transmission of torque, from the auxiliary tool onto the medical instrument or implant.

In a preferred embodiment, the connection means of the transfer element form a closure mechanism, more particularly a bayonet closure, with the corresponding connection means of the housing. The closure mechanism is unlocked by rotating, clamping or screwing. In a preferred embodiment, the closure mechanism, more particularly the bayonet closure, is unlocked by rotating the transfer element with respect to the housing. The closure mechanism, more particularly the bayonet closure, ensures that the medical instrument or implant does not inadvertently drop out of the housing. The closure mechanism, more particularly the bayonet closure, thus forms at least part of a transport safety device of the container for safely transporting and storing the implant. Moreover, the bayonet closure can easily be released by hand and thus allows simple and uncomplicated removal of the implant.

In a preferred embodiment of the transfer element according to the invention, the connection means of the connection section of the adapter segment comprise at least one groove in the outer lateral surface, preferably two grooves running at least partly diametrically. The at least one groove is intended to interact with the corresponding connection means of the housing and, more particularly, respectively hold one guide projection of the housing in order thus to form a closure mechanism, more particularly a bayonet closure.

The preferably two grooves in the transfer element can be interconnected such that the two grooves are embodied as a single groove that is intended to hold two guide projections of the housing. The two grooves preferably each have an open end closer to the first end of the transfer element and are interconnected in the circumferential direction on the connection section closer to the second end of the transfer element.

In a preferred embodiment, the connection means of the connection section comprise at least one guide projection on the outer lateral surface, preferably two guide projections that are at least approximately opposite one another in the circumferential direction. The at least one guide projection is intended to interact with the corresponding connection means of the housing, more particularly engage into respectively one groove in the housing, in order thus to form the closure mechanism, more particularly the bayonet closure.

The present invention likewise comprises embodiments of the transfer element in which the connection means of the connection section comprise both at least one groove and also at least one guide projection. The connection means of the connection section are intended to interact with the corresponding connection means of the housing. In one embodiment of the transfer element, which for example has a groove and a guide projection, the groove in the connection section holds a guide projection of the housing and the guide projection of the connection section engages into a groove in the housing. An advantage of this embodiment is that the rotational alignment of the transfer element relative to the housing is predetermined and that, during a removal of the transfer element and a subsequent renewed insertion of the transfer element into the housing, the same alignment of the transfer element—and hence of the medical instrument or implant—is ensured.

The housing preferably has an open end face and a longitudinal axis, which, in the connected state, runs at least approximately parallel to the longitudinal axis of the transfer element. In a preferred embodiment, the transfer element is, in the connected state, mounted on the housing such that the holder segment is easily accessible from the outside and more particularly protrudes from the open end face of the housing. The means for handling, more particularly the means for handling by hand, are preferably arranged on the holder segment in this case. Hence, the holder segment preferably serves as a handle for securely holding and actuating the transfer element. In order to remove the medical instrument or implant, the transfer element is, starting from the connected and locked state, preferably picked up on the holder segment in a first step and then rotated about its longitudinal axis and relative to the housing in order to unlock the closure mechanism, more particularly the bayonet closure. The connection means of the transfer element also interact with the corresponding connection means of the housing in this unlocked state. In a second step, the transfer element is partly pulled out of the housing along the longitudinal axis of the latter. The guide projections or the grooves of the transfer element also interact with the grooves or the guide projections of the housing in this pulled-out state. In a third step, the transfer element is removed from the housing together with the medical instrument or implant. To this end, the transfer element is lifted out of the housing in one movement corresponding to the profile of the grooves, preferably approximately perpendicularly to the longitudinal axis of said housing.

In a preferred embodiment, the transfer element has two guide projections, which are arranged at least approximately diametrically and are substantially circular cylindrical, conical or hemispherical. The round or roundish shape of the base area or of a cross section of the two guide projections initially affords the possibility of being able to pivot the transfer element about a pivot axis, which is perpendicular to the longitudinal axis of the transfer element and runs through the two guide projections, in order to remove the medical instrument or implant from the housing. Hence, the longitudinal axis of the transfer element is rotated with respect to the longitudinal axis of the housing, and the medical instrument or implant is lifted out of the housing, with the contact between the guide projections and the grooves in the housing being maintained and the connection means therefore still being able to interact. While the transfer element is being pivoted, the two guide projections of the transfer element serve as hinge points of the rotational axis. The transfer element is thereupon completely removed from the housing by removing the guide projections of the transfer element from the grooves by a movement corresponding to the profile of the grooves in the housing, preferably approximately perpendicularly to the longitudinal axis of the housing. As a result, said embodiment allows a safe removal of the medical instrument or implant from the housing, during which the risk of contamination of or damage to the implant surface as a result of undesired contact with other materials, in particular from the housing, is reduced because the medical instrument or implant was already at least partly pivoted out of the housing at the time at which the guide projections are removed from the grooves.

In a preferred embodiment of the transfer element, the adapter end region is embodied such that the contact area between the transfer element and the medical instrument or implant is minimal. The adapter end region of the adapter segment is preferably equipped with spring fingers, which have lugs. The lugs form rest faces for the implant. The implant is supported and held on these rest faces. By way of example, these grip under a body part of an integral implant and correspondingly hold the latter in an interlocking fashion. As a result, the transfer element ensures that particularly sensitive surfaces of the medical instrument or implant, such as e.g. the surface of the endosteal region of an implant, i.e. the region that is in direct contact with the bone in the implanted state, do not have contact areas with the transfer element itself or with the housing of the container.

In general, sterilization of contact areas between two elements is made more difficult by the fact that a sterilization means, such as e.g. ethylene oxide gas, water vapor or $H_2O_2$ does not reach these contact areas as well as regions that are not in contact with another element and hence are freely accessible to a liquid or a gas. Hence, an advantage of minimizing the contact area between the transfer element and the medical instrument or implant is that the sterilization process is thereby made simpler. A smaller design of the contact area leads to smaller areas that are awkward for complete sterilization and the risk of side effects, caused by poor or incomplete sterilization, can accordingly be minimized.

Said design of the adapter end region with spring fingers allows secure holding of the medical instrument or implant, even though only a small area of the medical instrument or implant contacts the transfer element. Hence, only a few regions of the medical instrument or implant are not freely accessible to the sterilization means, and good sterilizability of the medical instrument or implant is ensured.

The present invention furthermore relates to a container for a medical instrument or for a medical implant, more particularly for a dental implant. The container comprises a housing and a transfer element according to the present invention. The container is characterized by the fact that it has a closure mechanism, which acts between the housing and the connection section of the transfer element.

In a preferred embodiment, the closure mechanism between the housing and the connection section comprises a bayonet closure. The latter guarantees a secure closure and can nevertheless be released very easily by hand. The closure mechanism could alternatively comprise a snap connection or a screw-in closure.

During transport and storage, the transfer element is usually inserted into the housing and the closure mechanism, more particularly the bayonet closure, is locked. The closure mechanism is unlocked by rotating, clamping or screwing. In a preferred embodiment, the closure mechanism comprises a bayonet closure, which is unlocked by rotating the transfer element.

There may be a plurality of contact points between the transfer element, more particularly the connection section, and the housing, particularly in the locked state.

If the transfer element is locked with the housing, the housing preferably interacts with the spring fingers of the adapter end region, which hold the medical instrument or implant, for example by virtue of the housing engaging around the spring fingers of the adapter end region. As a result, the clamping force of the spring fingers is increased, and undesired releasing of the medical instrument or implant from the transfer element is prevented, particularly during transport.

The container according to the invention ensures that the medical instrument or implant, and more particularly the endosteal region of a dental implant, does not have contact areas with the housing. This prevents contamination of or damage to the implant by the housing.

The housing of the container according to the invention preferably comprises an open end face and a longitudinal axis. The transfer element is accessible from the outside thanks to the open end. The housing preferably substantially has the shape of a hollow cylinder, more particularly of a hollow cuboid or hollow circular cylinder. In a particularly preferred embodiment, the housing of the container according to the invention has the shape of a hollow cylinder with a circular cylindrical interior and with an inner lateral face. A circular cylindrical interior is particularly preferred in combination with at least one groove in the inner lateral face of the housing.

In a preferred embodiment, the housing of the container according to the invention has a longitudinal opening. Said opening preferably extends from the open end face to further than halfway down the housing in the direction of the opposite end of the housing. In the circumferential direction, the opening preferably does not extend over more than half of the circumference of the housing surface. The opening serves to remove the transfer element and the medical instrument or implant such that the removal of the medical instrument or implant need not, or need not exclusively, be through the open end face of the housing.

In a preferred embodiment, at least one groove is formed on the inner lateral face as a connection means of the housing. In a particularly preferred embodiment, at least two approximately diametrically opposed grooves are formed, which serve to interact with corresponding connection means of the transfer element, more particularly to hold a guide projection of the transfer element each, in order thus to form the bayonet closure.

In a particularly preferred embodiment, the at least one groove in the housing is embodied as a passage groove, i.e. the groove comprises an opening in the housing in the radial direction. However, alternatively it is also possible for the groove to be embodied as a recess without an opening in the inner lateral face of the housing.

In a preferred embodiment, the at least one groove in the housing has a closed and an open end. The closed end is preferably the end situated further away from the open end face of the housing than the open end of the groove. In the locked state of the container, the guide projection of the transfer element preferably comes to rest in the closed end of the groove. Accordingly, the open end is preferably the end situated closer to the open end face of the container. The open end of the groove preferably opens out in the direction of the longitudinal opening of the housing. The open end of the groove makes it possible to remove the guide projection of the transfer element from the groove in a simple fashion, or to insert the guide projection into the groove in a simple fashion.

In a particularly preferred embodiment, the at least one groove is designed as a passage groove and has an open end.

In a preferred embodiment, the housing has at least one guide projection on the inner lateral face as a connection means for the housing. In a particularly preferred embodiment, two guide projections are formed, which are at least approximately situated on a straight line perpendicular to the longitudinal axis and serve to engage into one groove in the transfer element each in order thus to form the bayonet closure.

In a preferred embodiment, the housing of the container according to the invention has said longitudinal opening for removing the medical instrument or implant and two guide projections, which are substantially circular cylindrical, conical or hemispherical. The round or roundish shape of the base area or of a cross section of the guide projections initially affords the possibility of being able to pivot the container about a pivot axis, which is perpendicular to the longitudinal axis of the housing and runs through the guide projections, in order to remove the housing from the implant. Hence, the longitudinal axis of the housing is rotated with respect to the longitudinal axis of the transfer element, and the medical instrument or implant is lifted out of the housing, with the contact between the housing and the transfer element being maintained and the connection means of the housing therefore still being able to interact with the corresponding connection means of the transfer element. During the pivoting, the guide projections of the housing or of the transfer element serve as hinge points of the pivot axis. The housing is thereupon completely removed from the transfer element and the medical instrument or implant by removing the guide projections of the housing or of the transfer element from the grooves by a movement corresponding to the profile of the grooves in the transfer element or in the housing. As a result, said embodiment of the container allows a safe removal of the medical instrument or implant from the housing, during which the risk of contamination of or damage to the implant surface as a result of undesired contact with other materials, in particular from the housing, is reduced because the medical instrument or implant was already at least partly removed from the housing at the time at which the guide projection is removed from the groove.

The container according to the invention preferably moreover comprises a medical instrument or implant, more particularly a dental implant, which is detachably attached to the transfer element and protected by the housing in the transport state.

The housing and the transfer element are preferably made of a biocompatible, sterilizable material so that sterilization can easily be carried out. In a particularly preferred embodiment, the material of the housing and the transfer element consists of stainless steel, ceramics, composite materials or, particularly preferably, of plastic, e.g. polyether ether ketone (PEEK), or titanium.

In a further preferred embodiment of the container, the transfer element and the housing in particular have a dimensionally stable design. The dimensional stability brings about optimum protection of the medical instrument or implant, particularly during transport, and thus leads to these being spared from damage.

Moreover, the housing preferably has a plurality of openings, more particularly slit-like holes, for better access of the sterilization medium to the surface of the medical instrument or implant.

The housing can also be considered to be a holding part for holding the transfer element and/or the medical instrument or implant.

For the purposes of transport and storage, the container according to the invention is preferably stored in a further, external packaging element which, inter alia, serves as a sterile barrier. Moreover, there may be further packaging elements such as cardboard boxes.

BRIEF DESCRIPTION OF THE DRAWINGS

In detail.

DETAILED DESCRIPTION

Figure 1:
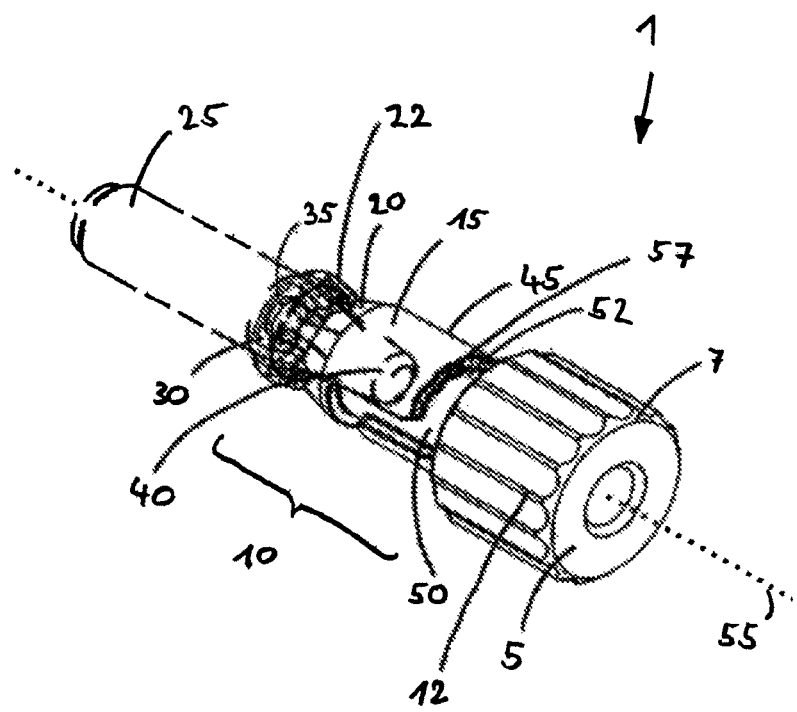
FIG. 1 shows a first embodiment of a transfer element according to the present invention, with a dental implant.

FIG. 1 shows a perspective illustration of a first embodiment of a transfer element 1 according to the present invention. The transfer element 1 comprises a holder segment 5 at a first end 7 and an adapter segment 10 connected to the holder segment 5. The holder segment 5 has ribs 12, which serve as means for handling the transfer element 1. With the aid of the ribs 12, the transfer element 1 can be securely picked up and held by hand.

The adapter segment 10 has a connection section 15 and an adapter end region 20, wherein the adapter end region 20 is arranged terminally at a second end 22 and the connection section 15 is arranged between the adapter end region 20 and the holder segment 5. A dental implant 25 has been mounted on the adapter end region 20 and it is illustrated by dashed lines in the figures. The adapter end region 20 is equipped with spring fingers 30, which have lugs 35. The lugs 35 form rest faces for the dental implant 25. The lugs 35 with the rest faces support and hold the dental implant 25 on the transfer element 1. FIG. 1 illustrates an integral dental implant 25 with a body part 40, behind which the lugs 35 of the adapter end region 20 engage and which is correspondingly held thereby. Hence only a small region of the dental implant 25 is in contact with the transfer element 1. The remaining regions of the dental implant 25, in particular the endosteal region, do not contact the transfer element and hence are freely accessible, for example for a sterilization means, which guarantees good sterilizability of the dental implant 25.

In the embodiment of the transfer element 1 illustrated in FIG. 1, the connection section 15 thereof has a substantially circular cylindrical design and has an outer lateral face 45. Formed into the outer lateral face 45 is a groove 50, which is part of connection means of the transfer element 1 and is intended to interact with the connection means of a housing of a container and form a bayonet closure. The two ends 52 of the groove 50 lie diametrically opposed on a plane perpendicular to a longitudinal axis 55 of the transfer element 1. Starting from the two ends 52 of the groove 50, the groove 50 initially runs anticlockwise in the circumferential direction. Then the groove 50 respectively describes an arc of 90° and runs parallel to the longitudinal axis 55 of the transfer element 1 in the direction of the adapter end region 20. Continuing, the groove 50 once again respectively describes an arc of 90°, with the groove 50 starting from one end 52 of the groove 50 now running clockwise and the groove 50 starting from the other end 52 running anticlockwise, in the circumferential direction.

In the vicinity of both ends 52, the groove 50 has arc-shaped widenings 57, which are intended to interact with connection means of a housing of a container in order to prevent inadvertent unlocking of the bayonet closure.

Figure 2A:
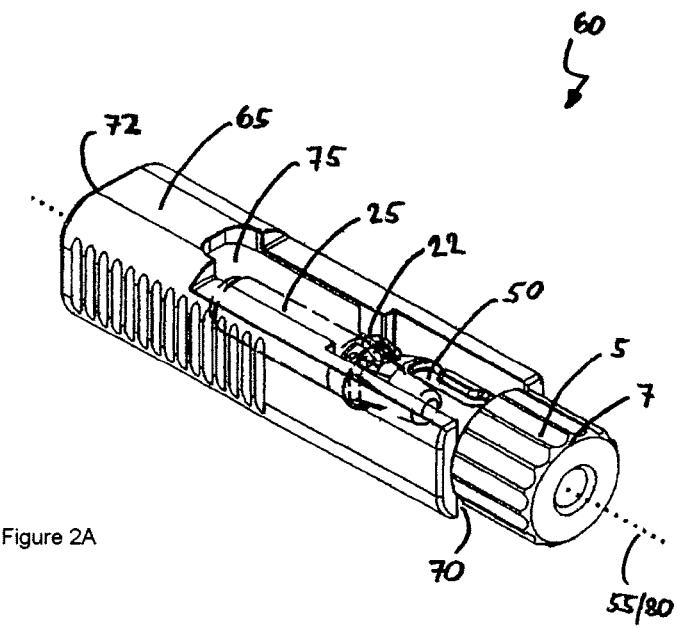
FIGS. 2A/B respectively show a perspective illustration and a plan view of a first embodiment of a container according to the invention, with the transfer element and the dental implant from FIG. 1, wherein the transfer element is in the inserted and locked state.
Figure 2B:
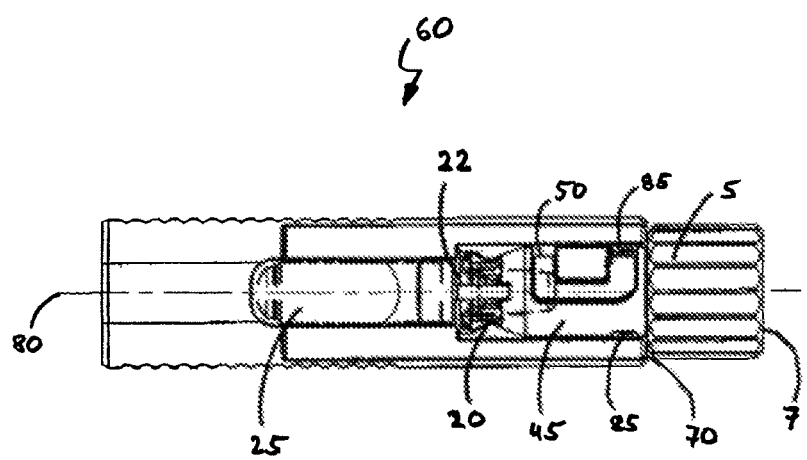

FIGS. 2A and 2B show illustrations of a first embodiment of a container 60 according to the invention, comprising the transfer element 1 as per FIG. 1, a housing 65 and the dental implant 25 from FIG. 1. As shown in FIG. 1, the dental implant 25 is attached to the transfer element 1. The transfer element 1 has been inserted into the housing 65 and locked with the housing 65 by means of a bayonet closure. The container 60 is preferably used for transport and storage of the dental implant 25 in this locked state.

FIG. 2A shows the container 60 in a perspective illustration. The housing 65 of the container 60 substantially has the shape of a hollow cuboid with rounded longitudinal edges. A first end face 70 of the housing 65 is open in order to hold the transfer element 1. A longitudinal side of the housing 65 has a longitudinal opening 75, which extends from the first end face 70 in the direction of the opposite end 72. Approximately two-thirds of said longitudinal side is open.

In the locked state, the longitudinal axis 55 of the transfer element 1 runs substantially parallel to a longitudinal axis 80 of the housing 65. The transfer element 1 is inserted into the housing 65 such that the first end 7 with the holder segment 5 is situated outside of the housing 65 and the second end 22 with the adapter end region 20 and the dental implant 25 attached thereto is situated within the housing 65. Hence, the holder segment 5 is easily accessible from the outside and can easily be picked up.

FIG. 2B shows a plan view of the container 60. In the vicinity of the open end face 70, two opposite sides respectively have one guide projection 85 on the inner lateral face 82 of the housing 65. The two guide projections 85 are situated on a straight line that is perpendicular to the longitudinal axis 80 of the housing 65. The two guide projections 85 engage in the groove 50 in the transfer element 1. In the locked state of the container 60 shown in FIG. 2, the guide projections 85 are situated in the diametrically opposing ends 52 of the groove 50 in the transfer element 1. Starting from the ends 52, the groove 50 initially runs in the circumferential direction. Hence the transfer element 1 cannot, with respect to the housing 65, be displaced along the longitudinal axis 80 in the locked state.

FIGS. 2 to 6 show the container 60 according to the invention at respectively different times during a removal of the transfer element 1 from the housing 65. By rotating the holder segment 5 by approximately 90° relative to the housing 65, the container 60 is transferred from the locked state illustrated in FIG. 2 into an unlocked state shown in FIG. 3.

Figure 3:
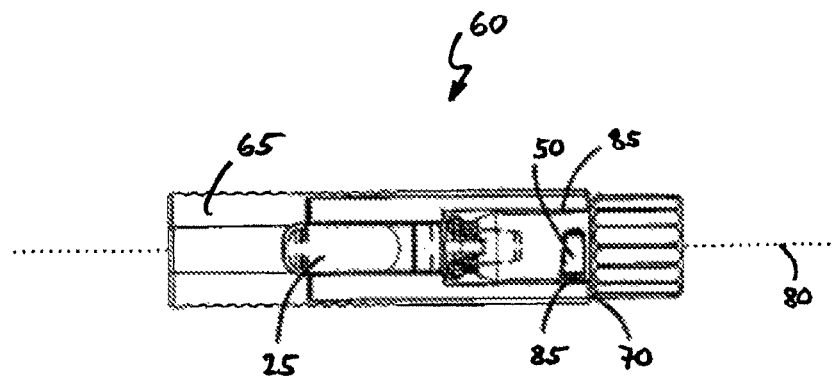
FIG. 3 shows the container from FIG. 2, wherein the transfer element is in the inserted and unlocked state.

FIG. 3 now shows the container 60 according to the invention from FIG. 2 in the unlocked state. The two guide projections 85 of the housing 65 are no longer situated at the two ends 52 of the groove 50 in the transfer element 1, but continue to interact with the groove 50. The next section of the groove 50 now runs parallel to the longitudinal axis 80 of the housing 65. By interacting with the guide projections 85 of the housing 65, the groove 50 allows the transfer element 1 to be partly pulled out of the open end face 70 of the housing 65 in the unlocked state by being pulled therethrough along the longitudinal axis 80 of the housing 65.

Figure 4:
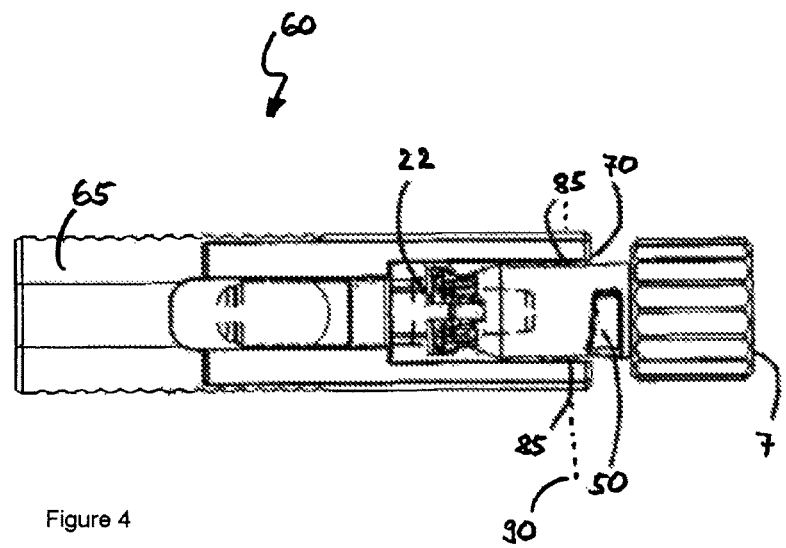
FIG. 4 shows the container from FIGS. 2 and 3, wherein the transfer element is partly pulled out.

FIG. 4 shows a plan view of the container 60 from FIG. 3, wherein the transfer element 1 is partly pulled through the open end face 70 of the housing 65. Here, the further profile of the groove 50 describes a change in direction and once again runs in the circumferential direction. By interacting with the guide projections 85 in the housing 65, the change in direction of the groove 50, forms a stop, which limits how far the transfer element 1 can be pulled out of the housing 65 in the longitudinal direction. The transfer element 1 can now be removed from the housing 65 by being lifted out at right angles to the longitudinal axis 80 of the housing 65. However, the transfer element 1 is preferably pivoted with respect to the housing 65 prior to the removal in order to simplify the removal of the transfer element 1.

The guide projections 85 of the shown housing 65 have a substantially circular cylindrical shape. The round base area of the guide projections 85 allows the guide projections 85 to act as hinge points that define a pivot axis 90, which runs perpendicular to the longitudinal axis 80 of the housing 65 and through the two guide projections 85. As a result of appropriate actuation of the holder segment 5, the longitudinal axis 55 of the transfer element 1 can be pivoted with respect to the longitudinal axis 80 of the housing 65 and the dental implant 25 attached to the second end 22 of the transfer element 1 is partly lifted out of the housing 65 through the longitudinal opening 75 in the housing 65.

Figure 5:
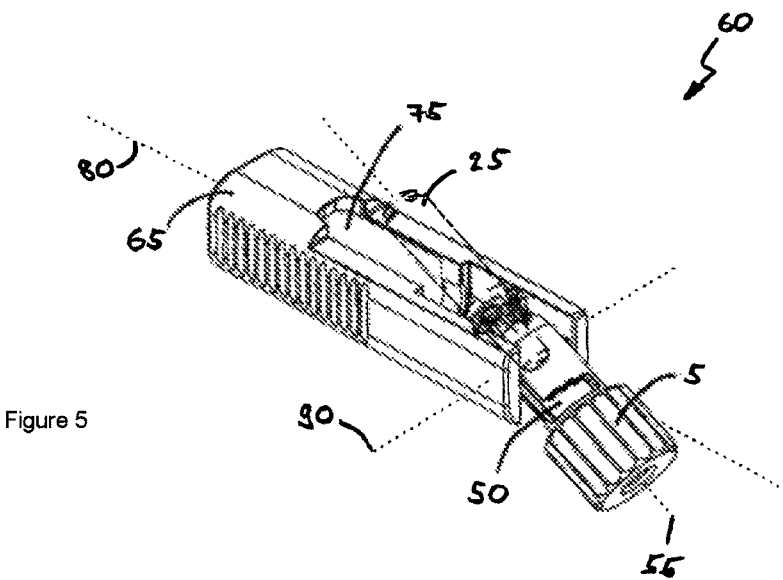
FIG. 5 shows the container from FIGS. 2 to 4, wherein the transfer element is in the pivoted state.

FIG. 5 shows the container 60 from FIG. 4, wherein the transfer element 1 is pivoted by about 35° with respect to the housing 65. That is to say the longitudinal axis 55 of the transfer element 1 is angled at about 35° with respect to the longitudinal axis 80 of the housing 65. This state allows a simple removal of the dental implant 25 by lifting the transfer element 1 through the longitudinal opening 75 of the housing 65 at an angle of 90° with respect to the longitudinal axis 55 of the transfer element 1, in accordance with the profile of the groove 50 in the transfer element 1. While the transfer element 1 is being lifted out, the guide projections 85 of the housing 65 are removed from the groove 50 in the transfer element 1. The pivoting out already removed most of the dental implant 25 from the housing 65. This makes safe removal of the dental implant 25 from the housing 65 possible, during which the risk of contamination of or damage to the implant surface as a result of undesired contact with the housing 65 is reduced.

The holder segment 5 moreover allows comfortable handling of the transfer element 1 during the whole process of removing the dental implant 25. In particular, the holder segment 5 of the transfer element 1 according to the invention allows a removal of the dental implant 25 from the housing 65 without the use of auxiliary tools; it can readily be carried out using only hands.

Figure 6:
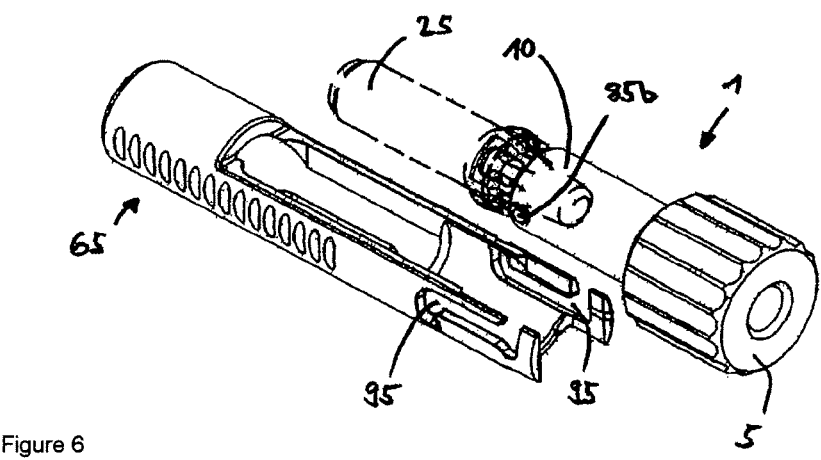
FIG. 6 shows a second embodiment of a container according to the invention, with a dental implant, wherein the transfer element is, together with the dental implant, removed from the housing.

FIG. 6 shows a second embodiment of a container 60 according to the invention, wherein a transfer element 1 as per a second embodiment is detachably connected to a dental implant 25 and separately present from a housing 65. In the embodiment shown in FIG. 6, the connection section 15 of the transfer element 1 has two guide projections 85b, which are each intended to interact with one groove in the housing 65. The housing 65 has a substantially circular cylindrical design. The housing 65 has two grooves 95, which are embodied as passage grooves in the present case and are intended to hold the two guide projections 85b of the transfer element 1.

Removing the dental implant 25 from a locked container 60 as per the embodiment shown in FIG. 6 is substantially carried out as per the steps explained in FIGS. 2 to 5. In particular, the illustrated embodiment likewise allows a removal of the dental implant 25 by pivoting the transfer element 1 with respect to the housing 65.

Figure 7:
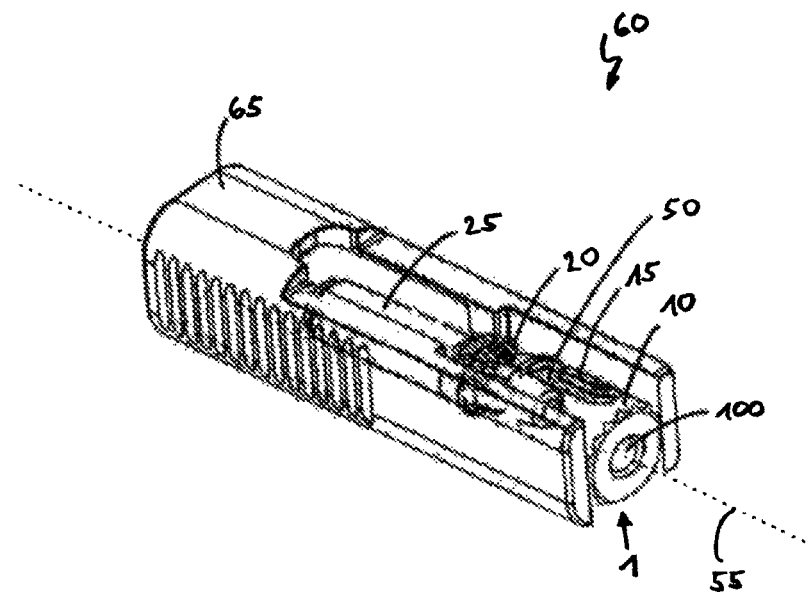
FIG. 7 shows a third embodiment of a container according to the invention, with a dental implant, in which the means for handling the dental implant are arranged on the inner side of the connection section.

FIG. 7 shows a third embodiment of a container 60 according to the invention, in which a transfer element 1 as per a third embodiment is detachably connected to a dental implant 25 and locked with a housing 65. The housing 65 corresponds to the embodiment shown in FIG. 2. The transfer element 1 contains a substantially circular cylindrical adapter segment 10. The adapter segment 10 has an adapter end region 20, a connection section 15 with a groove 50 and a substantially circular cylindrical opening 100 along the longitudinal axis 55 of the transfer element 1. The adapter end region 20 and the connection section 15 are embodied as per the embodiment shown in FIG. 2. The shown third embodiment of the transfer element does not comprise a holder segment. Means for handling (not illustrated) the transfer element 1 are arranged in the opening 100 along the longitudinal axis 55 and level with the connection section 15, and serve to hold an auxiliary tool. The auxiliary tool is inserted through the opening 100 into the connection section 15 and there it interacts with the means for handling the transfer element 1. By way of example, the means can have the shape of an internal polygon, in particular an internal hexagon or internal octagon, an internal Torx, a snap connection or a female thread. The auxiliary tool can be used to remove the transfer element 1 from the housing 65 together with the dental implant 25. The removal can be brought about substantially as described above, by rotating, pulling, pivoting the transfer element 1 and removing the housing 65. The dental implant 25 can subsequently be inserted into an implantation site with the aid of the transfer element 1 and the auxiliary tool.

Figure 8:
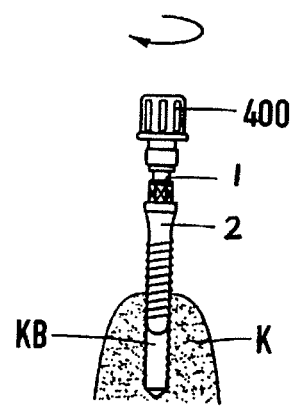
FIG. 8 shows a ratchet adapter (auxiliary tool) attached to the transfer element during insertion of the implant into the bone.

FIG. 8 shows a ratchet adapter 400, as one embodiment of an auxiliary tool, attached to the transfer element 1, which in turn is attached to an implant 2, whereby the ratchet adapter will be taken hold of by hand and rotated and the implant 2 will be received into a bone KB which has been prepared in the bone K (as described in U.S. Pat. No. 6,261,097 the entire disclosure of which is hereby incorporated by reference).

The invention claimed is:

1. A transfer element for a medical instrument or implant, more particularly for a dental implant, comprising a longitudinal axis, a first end, a second end, an adapter segment, arranged on the second end, for holding the medical instrument or implant and for attaching the transfer element to a housing of a container, and also comprising means for handling the medical instrument or implant by hand and/or with the aid of an auxiliary tool, wherein the first end, the second end, and the adapter segment are arranged on the longitudinal axis and the adapter segment has an adapter end region arranged on the second end, for detachably holding the medical instrument or implant and a connection section, arranged between the adapter end region and the first end, having connection means that interact with corresponding connection means of the housing, wherein the means for handling the medical instrument or implant are arranged on the first end, and the connection means of the transfer element form a bayonet closure with the corresponding connection means of the housing, the bayonet closure is constituted such that the transfer element is removed from the housing by rotating the transfer element with respect to the housing.

2. The transfer element as claimed in claim 1, wherein the transfer element has a holder segment arranged on the first end and connected to the adapter segment, and the means for handling the medical instrument or implant are arranged on the holder segment.

3. The transfer element as claimed in claim 1, wherein the means for handling the medical instrument or the implant are suitable for inserting a dental implant into an implantation site by hand and/or by means of an auxiliary tool.

4. The transfer element as claimed in claim 1, wherein the means for handling the medical instrument or implant are selected from the group consisting of ribs, notches, a handle, a screw thread, an internal or external Torx, a slit and an internal or external polygon and combinations thereof.

5. The transfer element as claimed in claim 1, wherein the transfer element is at least substantially designed as a hollow circular cylinder and the transfer element makes direct interaction between the medical instrument or implant and the auxiliary tool.

6. The transfer element as claimed in claim 1, wherein the connection means of the connection section comprise at least one groove, on an outer lateral face of the connection section, which groove serves to hold at least one guide projection of the housing, as corresponding connection means in order thus to form the bayonet closure.

7. The transfer element as claimed in claim 1, wherein the connection means of the connection section comprise at least one guide projection, on an outer lateral face of the connection section, which guide projection serves to engage into at least one groove in the housing, as corresponding connection means in order thus to form the bayonet closure.

8. The transfer element as claimed in claim 7, wherein the connection section has two at least approximately diametrical, substantially circular cylindrical or conical guide projections, wherein the two guide projections are, by interacting with two grooves in the housing, serve as hinge points of a pivot axis in order at least partly to pivot the implant out of the housing.

9. The transfer element as claimed in claim 1, wherein the adapter end region is equipped with spring fingers, which have lugs that hold the medical instrument or implant on rest faces that are formed by the lugs.

10. A container for a medical instrument or implant, more particularly for a dental implant, comprising a housing and a transfer element as claimed in claim 1, wherein the container has a closure mechanism, which acts between the housing and the connection section of the transfer element.

11. The container as claimed in claim 10, wherein the housing comprises an open end face and a longitudinal axis, and substantially has the shape of a hollow cylinder with an inner lateral face.

12. The container as claimed in claim 10, wherein the housing has a longitudinal opening for removing the medical instrument or implant.

13. The container as claimed claim 11, wherein the housing has a circular cylindrical interior and, on the inner lateral face, at least one groove, which serves to hold at least one guide projection of the transfer element to form the bayonet closure, wherein the connection means of the connection section comprise the at least one guide projection, on the outer lateral face, which projection serves to engage into at least one groove in the housing as corresponding connection means in order thus to form the bayonet closure.

14. The container as claimed in claim 13, wherein the at least one groove-is embodied as a passage groove or passage grooves.

15. The container as claimed in claim 11, wherein the housing has at least one guide projection on the inner lateral face thereof, which projection serves to engage into at least one groove of the transfer element to form the bayonet closure, wherein the connection means of the connection section comprise the at least one groove, which groove serves to hold at least one guide projection of the housing as corresponding connection means in order thus to form the bayonet closure.

16. The container as claimed in claim 12, wherein the container has two guide projections, which are substantially circular cylindrical or conical, wherein the guide projections are attached to the transfer element and/or to the housing and to serve as hinge points of a pivot axis in order at least partly to pivot the medical instrument or implant out of the housing through the longitudinal opening.

17. The transfer element of claim 6, comprising two grooves running partly diametrically on the outer lateral face which hold two guide projections of the housing.

18. The transfer element of claim 7, comprising two at least approximately diametrical guide projections on the outer lateral face which guide projections engage into the two grooves.

19. A transfer element for a medical instrument or implant, more particularly for a dental implant, comprising a longitudinal axis, a first end, a second end, an adapter segment, arranged on the second end, for holding the medical instrument or implant and for attaching the transfer element to a housing of a container, and also comprising means for handling the medical instrument or implant by hand and/or with the aid of an auxiliary tool, wherein the first end, the second end, and the adapter segment are arranged on the longitudinal axis and the adapter segment has an adapter end region arranged on the second end, for detachably holding the medical instrument or implant and a connection section, arranged between the adapter end region and the first end, having connection means that interact with corresponding connection means of the housing, wherein the means for handling the medical instrument or implant are arranged on the first end, and wherein the connection section has two at least approximately diametrical, substantially circular cylindrical or conical guide projections, wherein the two guide projections are, by interacting with two grooves in the housing, serve as hinge points of a pivot axis in order at least partly to pivot the implant out of the housing.

20. A container for a medical instrument or implant, more particularly for a dental implant, comprising a housing and a transfer element, the transfer element comprising:
  a longitudinal axis, a first end, a second end, an adapter segment, arranged on the second end, for holding the medical instrument or implant and for attaching the transfer element to a housing of a container, and also comprising means for handling the medical instrument or implant by hand and/or with the aid of an auxiliary tool, wherein the first end, the second end, and the adapter segment are arranged on the longitudinal axis and the adapter segment has an adapter end region arranged on the second end, for detachably holding the medical instrument or implant and a connection section, arranged between the adapter end region and the first end, having connection means that interact with corresponding connection means of the housing, wherein the means for handling the medical instrument or implant are arranged on the first end, and
  wherein the container has a closure mechanism, which acts between the housing and the connection section of the transfer element, and wherein the housing has a longitudinal opening for removing the medical instrument or implant, and wherein the container has two guide projections, which are substantially circular cylindrical or conical, wherein the guide projections are attached to the transfer element and/or to the housing and to serve as hinge points of a pivot axis in order at least partly to pivot the medical instrument or implant out of the housing through the longitudinal opening.

* * * * *

UNITED STATES PATENT AND TRADEMARK OFFICE
CERTIFICATE OF CORRECTION

| | |
|---|---|
| PATENT NO. | : 8,985,331 B2 |
| APPLICATION NO. | : 13/387023 |
| DATED | : March 24, 2015 |
| INVENTOR(S) | : Guenter et al. |

It is certified that error appears in the above-identified patent and that said Letters Patent is hereby corrected as shown below:

In the Claims

In column 14, line 31 delete "are."

Signed and Sealed this
Fourteenth Day of July, 2015

Michelle K. Lee
*Director of the United States Patent and Trademark Office*

UNITED STATES PATENT AND TRADEMARK OFFICE
CERTIFICATE OF CORRECTION

PATENT NO.          : 8,985,331 B2                                        Page 1 of 1
APPLICATION NO.     : 13/387023
DATED               : March 24, 2015
INVENTOR(S)         : Guenter et al.

It is certified that error appears in the above-identified patent and that said Letters Patent is hereby corrected as shown below:

In the Claims

In column 14, line 61 delete second instance of "to."

Signed and Sealed this
Twenty-first Day of July, 2015

Michelle K. Lee
*Director of the United States Patent and Trademark Office*